(12) United States Patent
Sablone

(10) Patent No.: US 11,554,053 B2
(45) Date of Patent: Jan. 17, 2023

(54) PROCESS FOR MAKING ARTICLES AND APPARATUS

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A., San Giovanni Teatino (IT)

( * ) Notice: Subject to any disclaimer, the term of this patent is extended or adjusted under 35 U.S.C. 154(b) by 560 days.

(21) Appl. No.: 16/585,075

(22) Filed: Sep. 27, 2019

(65) Prior Publication Data
US 2020/0100950 A1 Apr. 2, 2020

(30) Foreign Application Priority Data

Oct. 1, 2018 (IT) .................. 102018000009010

(51) Int. Cl.
*A61F 13/15* (2006.01)
*A61F 13/49* (2006.01)
*A61F 13/496* (2006.01)
*A61F 13/56* (2006.01)

(52) U.S. Cl.
CPC .. *A61F 13/15723* (2013.01); *A61F 13/15756* (2013.01); *A61F 13/496* (2013.01); *A61F 13/49009* (2013.01); *A61F 13/5622* (2013.01)

(58) Field of Classification Search
CPC ......... A61F 13/15723; A61F 13/15756; A61F 13/49009; A61F 13/496; A61F 13/5622
See application file for complete search history.

(56) References Cited

U.S. PATENT DOCUMENTS 6,432,248 B1    8/2002  Popp et al.
2005/0113793 A1*  5/2005  Bianco .............. A61F 13/15756
                                                    604/391

FOREIGN PATENT DOCUMENTS

EP         2025311 A1    2/2009

OTHER PUBLICATIONS

Search Report dated Mar. 8, 2019. 7 pages.

* cited by examiner

*Primary Examiner* — Vishal I Patel
(74) *Attorney, Agent, or Firm* — RMCK Law Group PLC

(57) ABSTRACT

A process and an apparatus for producing hygienic absorbent articles provided with at least one refastenable side seam from a chain of articles being formed having a first elastic sheet and a second elastic sheet, wherein the process and the apparatus are configured to perform operations on one or both of the elastic sheets in a cross direction, that is, with the elastic sheets parallel to the machine direction.

9 Claims, 3 Drawing Sheets

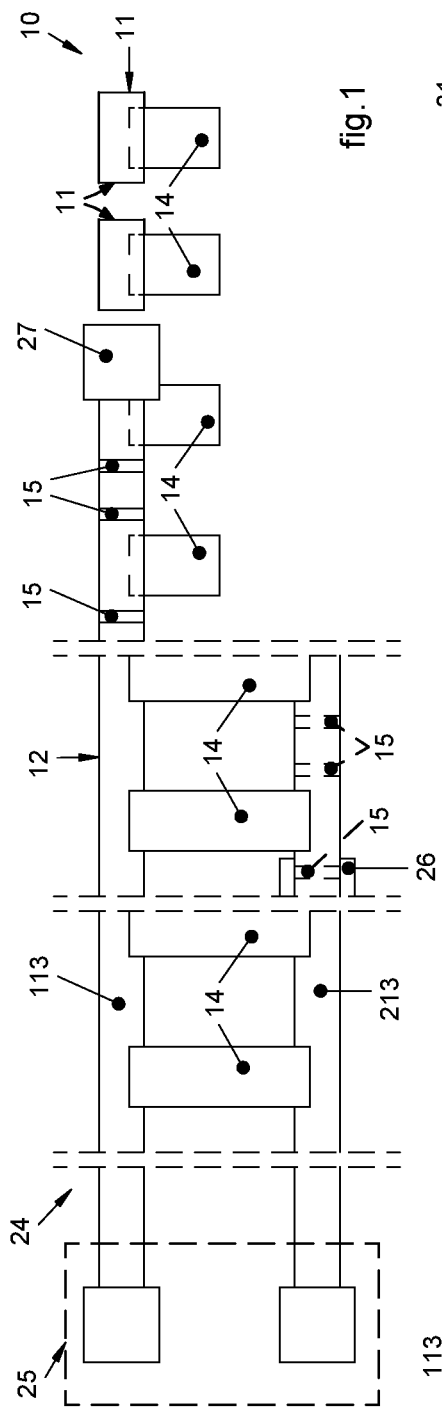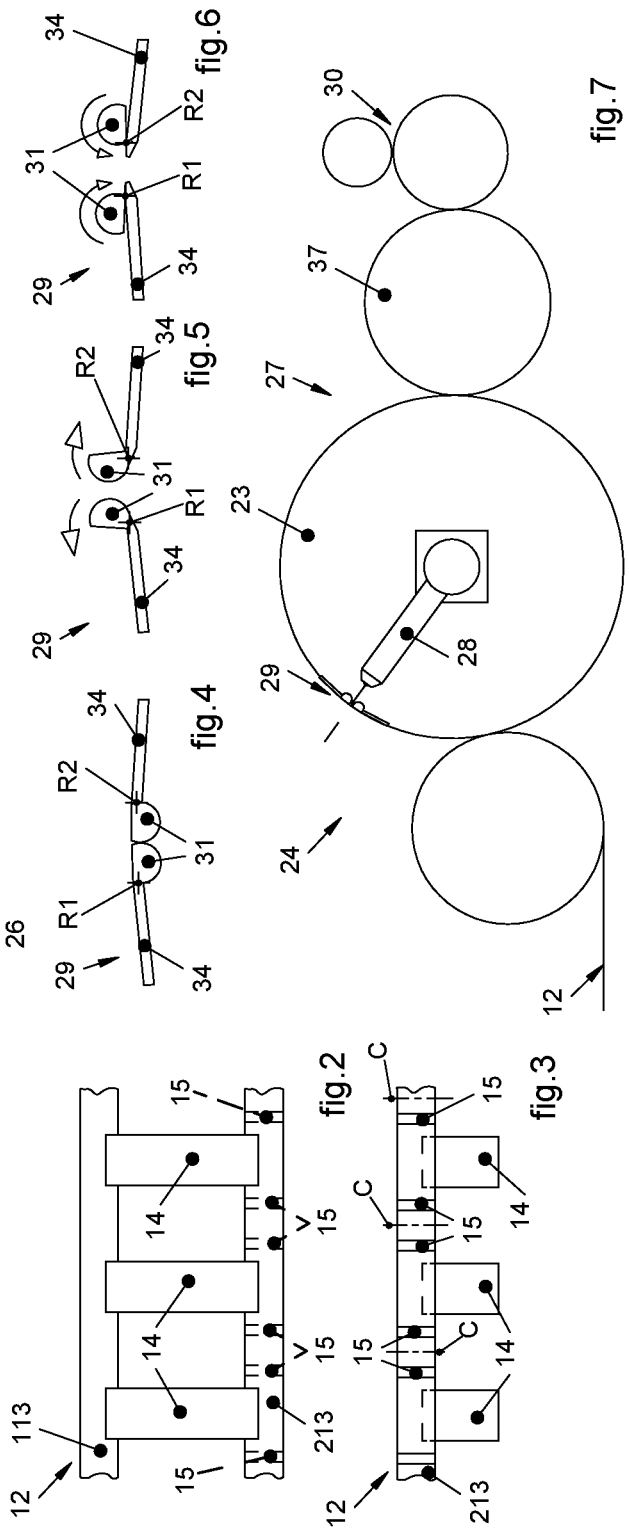

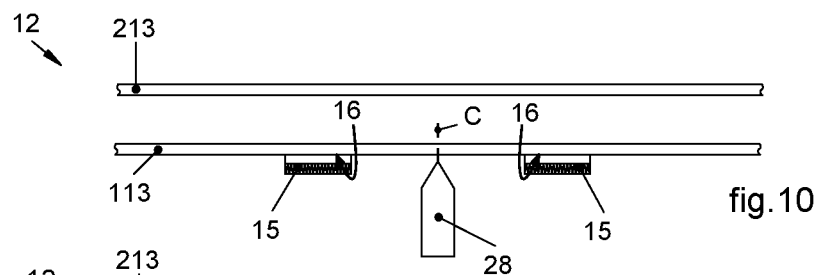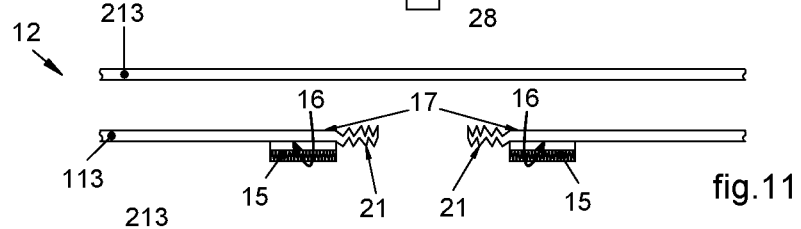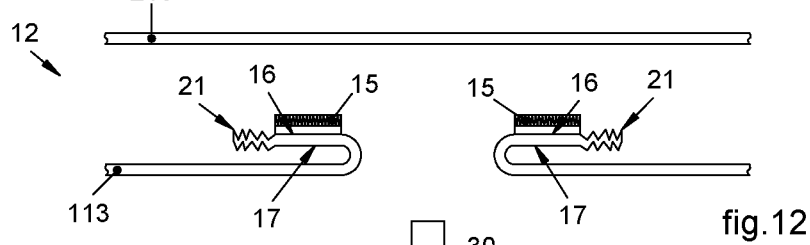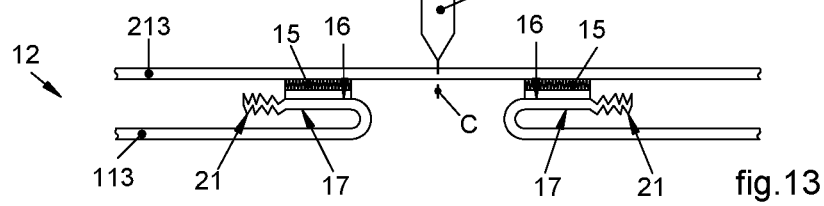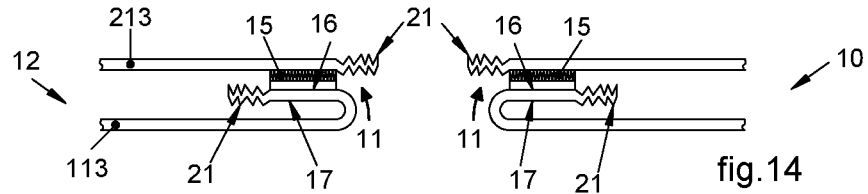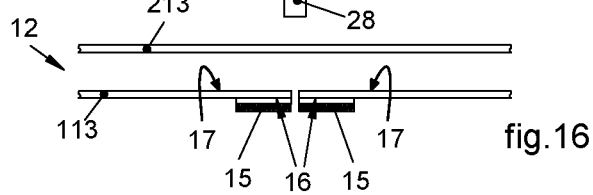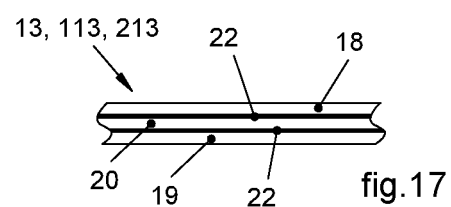

PROCESS FOR MAKING ARTICLES AND APPARATUS

CROSS-REFERENCE TO RELATED APPLICATION

This application claims priority to Italian Patent Application No. 102018000009010 filed Oct. 1, 2018. The disclosure of the above application is incorporated herein by reference in its entirety.

TECHNICAL FIELD

Embodiments of the present invention relate to a process for making hygienic absorbent articles provided with at least one refastenable side seam from a chain of articles being formed. The hygienic absorbent articles may comprise for example a diaper, a training pant, an incontinence diaper, a sanitary towel, or other articles intended to absorb bodily fluids.

Here and below, by refastenable side seam it is meant any refastenable seam suitable for connecting two portions of a hygienic absorbent article in a removable manner, said refastenable seam also being called a "reclosable side seam", or "refastenable side seam" in the sector.

Embodiments of the present invention also relate to an apparatus for making hygienic absorbent articles provided with at least one refastenable side seam.

BACKGROUND ART

It is known to make hygienic absorbent articles provided with refastenable side seams from a chain of articles being formed which is advanced along a machine direction, the articles being formed having their longitudinal axis positioned parallel to the machine direction.

That production technique is called "machine direction" which in the sector is distinguished from another technique called "cross direction", in which the hygienic absorbent articles are made while they are advanced with their longitudinal axis transversal to the machine direction.

Possible cross direction implementations provide for the use of a chain of articles being formed comprising two elastic sheets which are parallel to and spaced from each other transversely to the machine direction, and a plurality of absorbent bodies associated with the elastic sheets orthogonally to the machine direction.

The two elastic sheets may be supplied separately, or they may be part of a single sheet which is shaped in order to form a plurality of leg openings between which the absorbent bodies of the individual articles are positioned orthogonally to the machine direction.

In the latter case, the two elastic sheets are part of the single sheet and correspond to its lateral portions substantially parallel to the machine direction and between which the absorbent bodies are positioned.

Here and below, by elastic sheet it shall be meant a lateral portion of the single shaped sheet, or an elastic sheet supplied separately and which is part of a chain of articles being formed which comprises two elastic sheets that are parallel and spaced transversely relative to the machine direction.

Depending on the specific implementation used, it is possible to make the refastenable side seams by applying suitable connecting elements on the chain of articles for each of the articles which it comprises.

The connecting elements may comprise conjugated hook and loop elements, which are also known by the brand name of Velcro® systems, adhesives, or other elements suitable for connecting two portions of an article to each other in a removable manner.

Those connecting elements may be directly associated with a portion of an article or may be associated with another connecting element conjugated thereto, in such a way as to connect two portions of an article to each other in a removable manner.

In order to separate the articles of the cross-direction chain of articles, it is necessary to make a plurality of transverse cuts relative to the machine direction, in such a way as to obtain a plurality of separate hygienic absorbent articles.

It is known that such cross-direction operations, in the case of absorbent hygienic articles provided with refastenable side seams, besides being particularly complex and subject to errors, are slow and very expensive in energy terms.

There are many technological impediments which do not allow the production of articles with refastenable side seams in a cross direction without defects and which are at the same time of high-performance in functional terms. Besides being complex and energy-intensive, the prior art apparatuses do not allow articles to be obtained at high production rates.

It is known that known processes have proved impractical and do not allow processing to be carried out in an efficient and precise way on one or both of the elastic sheets, considering the position of the elastic sheets relative to each other.

In this context, it is not rare to find articles provided with refastenable side seams that are imprecise or with defects in terms of both position and operation.

Many known processes provide for the presence of scrap which may be removed, or may be kept on the article.

Should the scrap be removed, that would require the presence of special dedicated removal units which, besides complicating the apparatus itself, need frequent maintenance and are also very expensive in both economic and energy terms.

In this context, at the expense of the wearability and aesthetic quality of the articles, some manufacturers are known to prefer keeping the scrap on the articles, thereby avoiding having to remove it.

The articles obtained in this way are not very ergonomic, since at the refastenable side seams the scrap reduces the wearability of the article and also hides the refastenable side seam itself which is not easily identified by the user, or by the parent if the article is a diaper.

It is known that if the scrap is kept on the articles it may obstruct, or even damage, some units of the production apparatus which, in the most serious cases, means having to interrupt production in order to restore optimum operating conditions.

A further problem is that in order to be able to make the refastenable side seams, it is necessary to first separate the individual articles from the chain of articles being formed and only then to make the refastenable side seams.

That involves slowing the production and requires specific units for handling each individual article so as to then be able to make the respective refastenable side seams on each one.

For the reasons set out herein and for other reasons, in this context the articles provided with refastenable side seams are normally made in the machine direction rather than in the cross direction.

Therefore, it is necessary to improve and provide a process for making hygienic absorbent articles provided with refastenable side seams and a related apparatus which overcome at least one of the disadvantages of the prior art.

One aim of the present invention is to provide a process for making hygienic absorbent articles provided with refastenable side seams which allows operations to be performed on one or both of the elastic sheets in the cross direction, that is to say, with the elastic sheets parallel to the machine direction.

Another aim of the present invention is to provide a process for making articles provided with refastenable side seams efficiently and rapidly, which at the same time guarantees a high level of precision in the production of the refastenable side seams.

A further aim of the present invention is to provide an apparatus for making articles provided with refastenable side seams which is able to produce the refastenable side seams while the articles are obtained from the chain of articles being formed.

Another aim of the present invention is to provide a hygienic absorbent article provided with refastenable side seams which are aesthetically pleasing, easily identifiable by the user and such that they do not reduce the wearability of the article.

It is also an aim of the present invention to provide a process for carrying out one or more operations, such as cutting and folding operations, in a precise way, avoiding damaging the articles being formed.

Another aim of the present invention is to provide an apparatus for carrying out one or more operations in a precise way, avoiding damaging the articles being formed.

In order to overcome the disadvantages of the prior art and to achieve these and further aims and advantages, the Applicant has studied, experimented and produced the present invention.

DISCLOSURE OF THE INVENTION

The present invention is described and characterized in the independent claims, whilst the dependent claims set out the other characteristics of the present invention or variants of the main solution idea.

According to the above-mentioned aims, the present invention relates to a process for making hygienic absorbent articles provided with refastenable side seams from a chain of articles being formed comprising a first elastic sheet and a second elastic sheet.

According to one aspect of the present invention, the process provides for:
 keeping the first elastic sheet and the second elastic sheet in extended condition and superimposed on each other;
 fixing at least one connecting element on a surface portion of the first elastic sheet, wherein the surface portion faces towards the outside of the assembly constituted by the first elastic sheet and second elastic sheet superimposed;
 cutting the first elastic sheet so as to obtain two end portions each provided with a respective connecting element;
 folding the end portions towards the inside of the assembly constituted by the first elastic sheet and second elastic sheet superimposed such that the connecting elements face towards the second elastic sheet;
 connecting the end portions to the second elastic sheet through the connecting elements;
 cutting the second elastic sheet so as to separate one of the articles from the chain of articles being formed, wherein the connecting element makes the refastenable side seam.

Thanks to that process it is possible to rapidly obtain hygienic absorbent articles provided with refastenable side seams made in a precise way considering the relative positions of the two elastic sheets.

That allows precise cutting of the elastic sheets and at the same time production of the refastenable side seams without the need to first completely separate the articles from the chain of articles being formed.

That process also allows the avoidance of production difficulties due to the connecting elements which in the prior art may be anchored on the elastic sheet before they are in the correct position.

According to possible embodiments, the process may provide for cutting the second elastic sheet after having connected the end portions to the second elastic sheet by means of the connecting elements.

According to possible embodiments, the process may provide for temporarily spacing the first elastic sheet and the second elastic sheet from each other while the end portions are folded.

According to possible embodiments, the process may provide for folding the end portions by superimposing them onto respective portions of the first elastic sheet, wherein the folded end portions are intended to be part of distinct hygienic absorbent articles.

According to possible embodiments, the process may provide for hiding the connecting element from the second elastic sheet while the end portions are folded.

According to possible embodiments, the process may provide for cutting the
 second elastic sheet so as to obtain two end portions which by retracting move away from each other.

According to possible embodiments, the process may provide for moving the first elastic sheet away from the second elastic sheet before cutting the first elastic sheet.

According to possible embodiments, the process may provide for performing the operations of cutting the first elastic sheet and of folding the end portions along a curved path.

According to possible embodiments, the process may provide for cutting the first elastic sheet along a cutting line passing through the connecting element.

According to possible embodiments, the process may provide for cutting the first elastic sheet along a cutting line positioned between two adjacent connecting elements.

According to possible embodiments, the present invention also relates to an apparatus for making hygienic absorbent articles provided with refastenable side seams from a chain of articles being formed comprising a first elastic sheet and a second elastic sheet.

According to possible embodiments, the apparatus comprises:
 a supply unit of the first elastic sheet and the second elastic sheet;
 means for keeping the first elastic sheet and the second elastic sheet in extended condition and superimposed on each other;
 an application unit configured to fix at least one connecting element on a surface portion of the first elastic sheet, wherein the surface portion faces towards the outside of the assembly constituted by the first elastic sheet and second elastic sheet superimposed;

a processing station comprising:
- a first cutting device configured to cut the first elastic sheet so as to obtain two end portions each provided with a respective connecting element;
- a folding device configured to fold the end portions towards the inside of the assembly constituted by the first elastic sheet and the second elastic sheet superimposed so that the connecting elements face towards the second elastic sheet, so as to connect the end portions to the second elastic sheet by means of the connecting elements;
- a second cutting device configured to cut the second elastic sheet so as to separate one of the articles from the chain of articles being formed, wherein the connecting element makes the refastenable side seam.

According to possible embodiments, the folding device may comprise at least one couple of bodies each comprising a respective resting surface for the end portions and configured to rotate around a respective axis of rotation and holding means coupled to the resting surfaces and suitable for selectively retaining the end portions on said resting surfaces.

According to possible embodiments, at least one of the bodies extends from the respective axis of rotation for a length greater than the distance between the first elastic sheet and the second elastic sheet.

According to possible embodiments, the first cutting device is configured to cut the first elastic sheet along a cutting line positioned between the couple of bodies.

According to possible embodiments, at least one of the bodies is configured to cooperate with the holding means to move the first elastic sheet close to the first cutting device.

According to possible embodiments, the processing station may comprise a drum on which at least the first cutting device and the folding device are installed in such a way as to perform the relative operations along a curved path. According to possible advantageous embodiments, the drum may rotate around an axis of rotation.

According to possible embodiments, the first cutting device may be positioned in the rotary drum in such a way as to cut the first elastic sheet radially and towards the outside of the rotary drum.

According to possible embodiments, the second cutting device may be positioned downstream of the folding device.

According to possible embodiments, the apparatus may comprise a coupling device configured to make the connecting elements of the end portions adhere to the second elastic sheet, in order to connect them together.

According to possible embodiments, the coupling device may comprise a roller suitable for pressing the second elastic sheet and the end portions against the rotary drum.

DESCRIPTION OF THE DRAWINGS

These and other features of the present invention will become apparent from the following description of non-limiting embodiments, provided by way of example only, with reference to the accompanying drawings, in which:

FIG. 1 schematically illustrates part of an apparatus for making hygienic absorbent articles provided with refastenable side seams according to one possible embodiment of the present invention;

FIGS. 2 and 3 schematically illustrate a portion of a chain of articles being formed in two steps of a process according to one possible embodiment of the present invention;

FIG. 4 to 6 schematically illustrate a folding device in three operating configurations according to one possible embodiment of the present invention;

FIG. 7 schematically illustrates part of an apparatus for making hygienic absorbent articles provided with refastenable side seams according to one possible embodiment of the present invention;

FIGS. 10 and 11 schematically illustrate a portion of a chain of articles being formed before and after the cutting of the first elastic sheet according to one possible embodiment of the present invention;

FIG. 12 schematically illustrates a portion of a chain of articles being formed after having folded the end portions of the first elastic sheet according to one possible embodiment of the present invention;

FIG. 13 schematically illustrates a portion of a chain of articles being formed after having connected the end portions to the second elastic sheet by means of the connecting elements and before performing the cutting of the second elastic sheet according to one possible embodiment of the present invention;

FIG. 14 schematically illustrates a portion of a chain of articles being formed and a portion of a hygienic absorbent article obtained from it and provided with a refastenable side seam according to one possible embodiment of the present invention;

FIGS. 15 and 16 schematically illustrate two possible variants of FIGS. 10 and 11;

FIG. 17 schematically illustrates a detail of an elastic sheet according to one possible embodiment of the present invention.

For clarity, where possible, identical reference numbers have been used to identify common elements which are identical in the figures. It shall be understood that elements and features of one embodiment may be appropriately incorporated in other embodiments without further explanation.

DESCRIPTION OF EMBODIMENTS OF THE INVENTION

Figure 8:
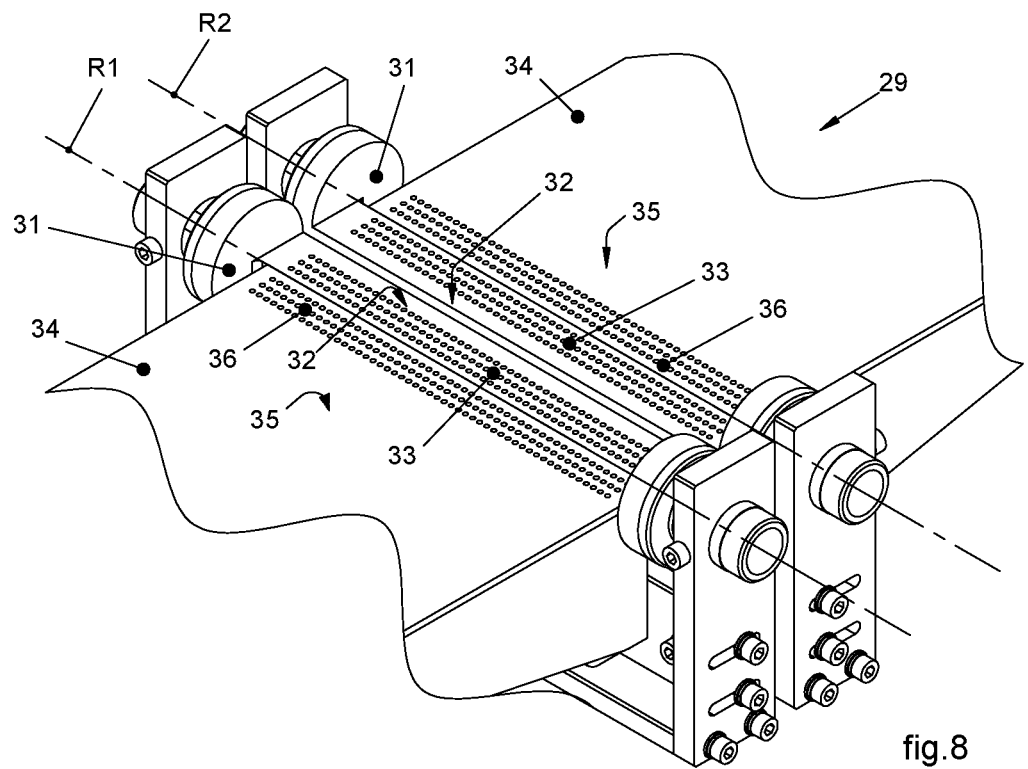
FIG. 8 illustrates a folding device according to one possible embodiment of the present invention.
Figure 9:
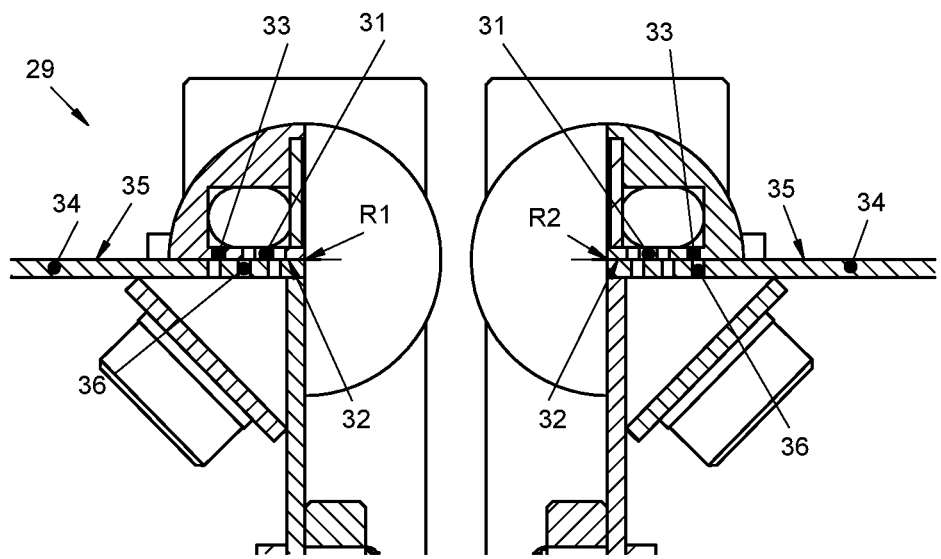
FIG. 9 illustrates a section of FIG. 8.

Embodiments described herein, with reference to the figures, relate to a process and an apparatus 24 for making hygienic absorbent articles 10 provided with at least one refastenable side seam 11 from a chain 12 of articles being formed.

The refastenable side seam 11 is suitable for connecting two portions of an article 10 in a removable manner, that is to say, in such a way that the article 10 can be opened/closed, separating/connecting two portions which are part of the latter.

Here and below, by the term "refastenable side seam" it is meant any refastenable seam, whether it is located in a lateral zone, or in another zone, of the article 10 as is commonly understood in the sector with reference to a "reclosable side seam", or "refastenable side seam".

The chain 12 may comprise two elastic sheets 13 with which a plurality of absorbent bodies 14 are associated, or a shaped continuous sheet comprising a plurality of leg openings between which the absorbent bodies 14 are positioned, or other types of assemblies which define a plurality of articles 10 being formed.

For the purpose of illustration and without thereby limiting the scope of the present invention to a specific type of chain 12 of articles being formed, hereinafter reference will be made to a chain 12 of articles being formed comprising a first elastic sheet 113 and a second elastic sheet 213.

According to possible embodiments, the first elastic sheet 113 and the second elastic sheet 213 may advance at least for one stretch along a respective direction parallel to the machine direction.

According to possible embodiments, the first elastic sheet 113 and the second elastic sheet 213 may advance at least for one stretch along a shared machine direction.

According to possible embodiments, the first elastic sheet 113 and the second elastic sheet 213 may be parallel to the machine direction, in such a way as to produce the hygienic absorbent articles 10 in cross direction.

According to possible embodiments of the present invention, it shall be understood that any operation carried out on one or more of the elastic sheets 113 and 213 may occur either while they are part of the chain 12 of articles being formed, or while they are separate from the latter.

According to possible embodiments, the present invention relates to a process which provides for:
  keeping the first elastic sheet 113 and the second elastic sheet 213 in extended condition and superimposed on each other;
  fixing at least one connecting element 15 on a surface portion 16 of the first elastic sheet 113, wherein the surface portion 16 faces towards the outside of the assembly constituted by the first elastic sheet 113 and the second elastic sheet 213 superimposed;
  cutting the first elastic sheet 113 so as to obtain two end portions 17 each provided with a respective connecting element 15;
  folding the end portions 17 towards the inside of the assembly constituted by the first elastic sheet 113 and second elastic sheet 213 superimposed such that the connecting elements 17 face towards the second elastic sheet 213;
  connecting the end portions 17 to the second elastic sheet 213 through the connecting elements 15;
  cutting the second elastic sheet 213 so as to separate one of the articles 10 from the chain 12 of articles being formed, wherein the connecting element 15 makes the refastenable side seam 11.

According to possible embodiments, the process provides that the first elastic sheet 113 be cut transversely to the machine direction.

According to possible embodiments, the process provides for the second elastic sheet 213 being cut transversely to the machine direction.

According to possible embodiments, illustrated in FIG. 17, the elastic sheet 13, the first elastic sheet 113 and the second elastic sheet 213 may each comprise a first layer 18 and a second layer 19 between which at least one elastic element 20 is coupled.

According to possible embodiments, the elastic element 20 may be an elastic thread, an elastic tape, or other similar elements, or an elastic layer, breathable at least to air, capable of giving elasticity to the elastic sheet 13.

For example, the elastic sheet 13 may comprise a plurality of elastic elements 20, whether they are elastic threads, elastic tapes, or combinations thereof, associated with a first layer 18 and a second layer 19 which comprise a non-extendible material, for example a non-woven material.

According to possible embodiments, the at least one elastic element 20 may be associated with the first layer 18 and with the second layer 19 in extended condition in such a way that the elastic sheet 13 in relaxed condition has a length which is less than that which it has in extended condition.

The elasticity provided by the elastic element 20 associated with the first layer 18 and with the second layer 19 in extended condition allows an elastic sheet 13 to be obtained which can be suitably processed to obtain one or more retracted portions 21 after a cut.

According to possible embodiments, the possible retracted portions 21 are positioned next to the respective surface portion 16.

According to possible embodiments, the at least one elastic element 20 may be associated with the first layer 18 and with the second layer 19 by gluing in extended condition.

According to possible embodiments, between the elastic element 20 and the first layer 18 and/or between the elastic element 20 and the second layer 19 there may be adhesive zones 22. For example, those adhesive zones 22 may comprise glue, or an adhesive material.

According to possible embodiments, the at least one elastic element 20 may be associated with the first layer 18 and with the second layer 19 by trapping it between them in extended condition by means of a suitable trapping pattern.

That trapping pattern may comprise a plurality of welds suitably positioned relative to the elastic element 20 for locally trapping the latter in extended condition, or relaxed condition.

In this way, the welds not only define the position of the elastic element 20 but also allow local definition of its elastic properties.

According to possible embodiments, the elastic sheet 13 may comprise at least one elastic portion.

According to possible embodiments, the elastic portion covers the entire extent of the elastic sheet 13.

According to possible embodiments, one of the elastic portions covers most of the extent of the elastic sheet 13.

According to possible embodiments, the elastic sheet 13 may comprise at least one elastic portion and at least one non-elastic portion, wherein the elastic portion comprises at least one elastic element 20, and the non-elastic portion is not provided with an elastic element 20, or is provided with an inhibited elastic element 20, that is to say, whose elastic properties are impeded, or considerably reduced. For example, the elastic element 20 may be inhibited by suitably trapping parts of it by means of a defined trapping pattern.

Such possible embodiments of an elastic sheet 13 may be used to obtain a hygienic absorbent article 10 comprising differentiated zones and provided with one or more retracted portions 21.

According to possible embodiments, the connecting element 15 may be fixed on a surface portion 16 of the first layer 18 and/or of the second layer 19 of the elastic sheet 13.

According to possible embodiments, the connecting element 15 may be fixed on the surface portion 16 by gluing, or by welding, in such a way as to obtain a connecting layer. Fixing the connecting element 15 by welding is advantageous, since there is no need to use glue.

By the term surface portion 16 it is meant the portion of the elastic sheet 13 which is connected to the connecting element 15. Depending on the cases, the surface portion 16 may be connected to part of the connecting element 15, in such a way that a portion of the connecting element 15 is not connected to the elastic sheet 13.

According to possible embodiments, the connecting element 15 may comprise a hook element, a loop element suitable for being connected to a conjugated hook element, an adhesive, or other elements suitable for connecting the portions of the hygienic absorbent articles 10 in a removable manner, wherein the portions are obtained from the elastic sheets 13 once the individual articles 10 have been separated from the chain 12 of articles being formed.

For example, the connecting element 15 may be configured to be removably associated with a portion of the article 10 directly, or by means of another connecting element 15.

According to possible embodiments, the connecting element 15 may project beyond the surface portion 16 so that the retracted portion 21 is at least partially hidden by the connecting element 15.

That aspect allows the retracted portion 21 to be at least partially hidden so that, besides not obstructing the refastenable side seam 11, it does not alter the aesthetic appearance and does not in turn hide the connecting elements 15 from the user who intends to open the article 10.

According to possible embodiments, should the retracted portion 21 have a length in relaxed condition that is less than or equal to the projecting portion of the connecting element 15, the retracted portion 21 could be completely hidden by the connecting element 16.

According to possible embodiments, should the retracted portion 21 have a length in relaxed condition that is greater than the projecting portion of the connecting element 15, the retracted portion 21 could be partially hidden by the connecting element 15.

According to possible embodiments, the first elastic sheet 113 may be cut transversely to the machine direction so as to obtain two end portions 17.

According to possible embodiments, the first elastic sheet 113 may be cut mechanically, for example with metal blades, rotary blades, or by means of a laser device, or by means of a thermal cutting device.

According to possible embodiments, the process may provide for cutting the second elastic sheet 213 after having connected the end portions 17 to the second elastic sheet 213 by means of the connecting elements 15.

That aspect has the advantage of sequentially making a refastenable side seam 11 of one article 10 together with another refastenable side seam 11 of another article 10.

According to possible embodiments, the second elastic sheet 213 may be cut transversely to the machine direction.

Therefore, at the moment of cutting the second elastic sheet 213 an article 10 is created which already has two refastenable side seams 11.

The primary advantage obtained is the production speed and in addition a reduced complexity of the process and the apparatus 24 compared with the prior art which comprises more handling units for each article which are provided with related folding devices for making any folds required.

According to possible embodiments, the process may provide for temporarily spacing the first elastic sheet 113 and the second elastic sheet 213 from each other while the end portions 17 are folded.

That aspect allows the end portions 17 to be folded while avoiding the possibility of the connecting elements 15 being accidentally anchored to the second elastic sheet 213.

According to possible embodiments, the process may provide for folding the end portions 17 by superimposing them onto respective portions of the first elastic sheet 113, wherein the folded end portions 17 are intended to be part of distinct hygienic absorbent articles 10.

That allows simultaneous production of two refastenable side seams 11 at a time of two distinct hygienic absorbent articles 10. That aspect allows to speed up the production of the articles 10, since it is not necessary to wait for completion of the refastenable side seams 11 of one article 10 before starting production of those of the next article 10.

According to possible embodiments, the process may provide for hiding the connecting element 15 from the second elastic sheet 213 while the end portions 17 are folded.

That aspect prevents the connecting elements 15 from getting caught on the second elastic sheet 213.

According to possible embodiments, the process may provide for cutting the second elastic sheet 213 so as to obtain two end portions 17 which by retracting move away from each other. With reference to the drawings, the portions retracted following a cut are labelled 21.

That aspect allows to considerably contain the extent of the end portions 17 following the cut, since they retract. That considerably reduces the possibility of difficulties occurring due to the presence of free portions during the production of the articles 10.

That aspect also allows to obtain a refastenable side seam 11 without the need to remove the scrap, and which does not compromise the wearability of the hygienic absorbent article 10, at the same time making the latter aesthetically pleasing.

That solution also allows to obtain a refastenable side seam 11 which is easily identifiable by a parent, or by the user, since the retracted portion 21 does not hide the connecting elements 15 of the refastenable side seam 11.

According to possible embodiments, the process may provide for moving the first elastic sheet 113 away from the second elastic sheet 213 before cutting the first elastic sheet 113.

That aspect allows only the first elastic sheet 113 to be moved towards the cutting device so as to only cut the latter without accidentally being able to also cut the second elastic sheet 213. Moreover, that aspect also allows to reduce the energy necessary to perform the cutting, since only one of the two elastic sheets 113 and 213 has to be cut.

According to possible embodiments, the process may provide for performing the operations of cutting the first elastic sheet 113 and of folding the end portions 17 along a curved path.

For example, it is possible to perform those operations on a drum 23 which allows to perform the operations and at the same time to change the orientation and direction of advancement of the chain 12 of articles being formed.

According to possible embodiments, the drum 23 may advantageously be a rotary drum.

According to possible embodiments, the process may provide for cutting the first elastic sheet 113 along a cutting line C passing through the connecting element 15.

That aspect allows the connecting element 15 to be separated into two parts so that each of them is positioned on a distinct end portion 17. That simplifies the step of fixing the connecting elements 15, since only one connecting element 15 is necessary in order to produce two refastenable side seams 11 of two distinct hygienic absorbent articles 10.

According to possible embodiments, the process may provide for cutting the first elastic sheet 113 along a cutting line C positioned between two adjacent connecting elements 15.

That aspect allows the edges of the connecting elements 15 to be kept well defined and requires less energy for the cutting, since it is not necessary to cut the connecting elements 15 in addition to the first elastic sheet 113.

According to possible embodiments, following the cutting of the first elastic sheet 113 it is possible to carry out further operations either on the first elastic sheet 113 cut, or on the second elastic sheet 213, as well as on both of the elastic sheets 113 and 213.

For example, it is possible to suitably fold, or reposition, the edges of the first elastic sheet 113 which has been cut.

According to possible embodiments, the connecting element 15 may project beyond the respective surface portion 16 so that the respective retracted portion 21 is at least partially hidden by the connecting element 15.

According to possible embodiments, the present invention also relates to an apparatus 24 for making hygienic absorbent articles 10 provided with refastenable side seams 11 from a chain 12 of articles being formed comprising a first elastic sheet 113 and a second elastic sheet 213.

According to possible embodiments, the apparatus 24 comprises:
  a supply unit 25 of the first elastic sheet 113 and the second elastic sheet 213;
  means for keeping the first elastic sheet 113 and the second elastic sheet 213 in extended condition and superimposed on each other;
  an application unit 26 configured to fix at least one connecting element 15 on a surface portion 16 of the first elastic sheet 113, wherein the surface portion 16 faces towards the outside of the assembly constituted by the first elastic sheet 113 and the second elastic sheet 213 superimposed;
  a processing station 27 comprising:
    a first cutting device 28 configured to cut the first elastic sheet 113 so as to obtain two end portions 17 each provided with a respective connecting element 15;
    a folding device 29 configured to fold the end portions 17 towards the inside of the assembly constituted by the first elastic sheet 113 and the second elastic sheet 213 superimposed so that the connecting elements 15 face towards the second elastic sheet 213, so as to connect the end portions 17 to the second elastic sheet 213 by means of the connecting elements 15;
    a second cutting device 30 configured to cut the second elastic sheet 213 so as to separate one of the articles 10 from the chain 12 of articles being formed, wherein the connecting element 15 makes the refastenable side seam 11.

According to possible embodiments, the folding device 29 may comprise at least one couple of bodies 31 each comprising a respective resting surface 32 for the end portions 17 and configured to rotate around a respective axis of rotation R1 and R2, and holding means 33 coupled to the resting surfaces 32 and suitable for selectively retaining the end portions 17 on the resting surfaces 32.

That aspect allows to have a folding device 29 suitable for independently retaining and folding two end portions 17 of two distinct hygienic absorbent articles 10.

According to possible embodiments, the folding device 29 may comprise a flat stretch 34 positioned at a respective body 31.

According to possible embodiments, the flat stretches 34 define a respective resting surface 35 and are provided with holding means 36 coupled to the resting surfaces 35 suitable for retaining a portion of the first elastic sheet 113, as well as a stretch of the first elastic sheet 113 folded on itself.

According to possible embodiments, as in FIG. 4, the bodies 31 may adopt at least one configuration in which the resting surface 32 is substantially coplanar with the resting surface 35 of the respective flat stretch 34 or slanted relative to the latter.

According to possible embodiments, illustrated in FIGS. 5 and 6, the bodies 31 rotating around respective axes of rotation R1 and R2 may adopt at least one configuration in which the resting surface 32 faces towards the resting surface 35 of the respective flat stretch 34.

According to possible embodiments, the holding means 33 and 36 may comprise a plurality of holes fluidly connected to suction means suitable for retaining the first elastic sheet 113 on the resting surface 32 and 35.

According to possible embodiments, at least one of the bodies 31 extends from the respective axis of rotation R1 and R2 for a length greater than the distance between the first elastic sheet 113 and the second elastic sheet 213.

During the rotation of the bodies 31, that aspect allows to prevent the connecting elements 15 from coming into contact with the second elastic sheet 213 and also allows the two elastic sheets 113 and 213 to be spaced from each other during the rotation of the end portions 17 of the first elastic sheet 113 without the need to use further additional separating devices.

According to possible embodiments, the initial distance between the first elastic sheet 113 and the second elastic sheet 213 may be defined before the cutting of the first elastic sheet 113 is performed.

According to possible embodiments, the first cutting device 28 is configured to cut the first elastic sheet 113 along a cutting line C positioned between the couple of bodies 31.

That aspect allows to speed up the production of the hygienic absorbent articles 10 and at the same time allows to cut and fold the end portions 17 in a precise way and with high production rates.

According to possible embodiments, at least one of the bodies 31 is configured to cooperate with the holding means 33 to move the first elastic sheet 113 close to the first cutting device 28.

That aspect allows to retain the first elastic sheet 113 and to move only this latter close to the first cutting device 28 so as to precisely cut only the first elastic sheet, without accidentally also cutting the second elastic sheet 213.

According to possible embodiments, the processing station 27 may comprise a drum 23 on which at least the first cutting device 28 and the folding device 29 are installed in such a way as to perform the relative operations along a curved path.

According to possible embodiments, the drum 23 may rotate around an axis of rotation which is orthogonal to the machine direction.

That aspect allows to speed up the operations of cutting and folding and at the same time to contain the dimensions of the devices and to modify the direction of advancement while performing the cutting and folding of the two end portions 17.

According to possible embodiments, the first cutting device 28 may be positioned in the drum 23 in such a way as to cut the first elastic sheet 113 radially and towards the outside of the drum 23.

That aspect allows containment of the dimensions since the first cutting device 28 is positioned in a space which is not used in the known apparatuses.

According to possible embodiments, the second cutting device 30 may be positioned downstream of the folding device 29.

That aspect allows the hygienic absorbent articles 10 to be separated from the chain 12 after having produced both of their refastenable side seams 11.

According to possible embodiments, the apparatus 24 may comprise a coupling device 37 configured to make the connecting elements 15 of the end portions 17 adhere to the second elastic sheet 213, in order to connect them together.

For example, a coupling device 37 may comprise a roller, or other compression element, suitable for making the connecting elements 15 adhere to the second elastic sheet 213 by pressing the latter towards the first elastic sheet 113.

According to possible embodiments, the coupling device 37 may comprise a roller suitable for pressing the second elastic sheet 213 and the end portions 17 against the drum 23.

According to possible embodiments, the means for holding the elastic sheets 113 and 213 may comprise pulling and/or suction devices. For example, such means may be configured to hold the elastic sheets 113 and 213 in extended condition and superimposed on each other by means of suction.

According to possible embodiments, the first cutting device 28 may comprise a mechanical cutting device, for example with a body provided with one or more blades, even rotary, or a laser cutting device, or a thermal cutting device.

According to possible embodiments, the second cutting device 30 may comprise a mechanical cutting device, for example an assembly formed by a roller provided with blades and a conjugated counter-knife, a unit provided with one or more blades, even rotary, or a laser cutting device, or a thermal cutting device.

According to possible embodiments, not illustrated, the apparatus 24 may comprise a folding unit configured to fold the chain 12 of articles being formed in such a way as to superimpose the two elastic sheets 113 and 213 on each other.

It is clear that the process and the apparatus 24 described above may be modified and/or have parts added, without thereby departing from the scope of the present invention.

It is also clear that, although the present invention has been described with reference to several specific examples, a person skilled in the art will certainly be able to make many other equivalent embodiments of the process and of the apparatus 24 having the features described in the claims and therefore all covered by the scope of protection that they define.

In the claims below, references in brackets are intended only to facilitate reading and must not be considered to be limiting factors as regards the scope of protection of the specific claims.

The invention claimed is:

1. A process for making hygienic absorbent articles provided with refastenable side seams from a chain of articles being formed having a first elastic sheet and a second elastic sheet, comprising:
   keeping said first elastic sheet and said second elastic sheet in extended condition and superimposed on each other;
   fixing at least one connecting element on a surface portion of said first elastic sheet, wherein said surface portion faces towards an outside of an assembly constituted by said first elastic sheet and said second elastic sheet superimposed;
   cutting said first elastic sheet so as to obtain two end portions each provided with a respective connecting element of said at least one connecting element;
   folding said end portions towards an inside of the assembly such that said respective connecting elements face towards said second elastic sheet;
   connecting said end portions to said second elastic sheet through said respective connecting elements; and
   cutting said second elastic sheet so as to separate one of said articles from said chain of articles being formed,
   wherein said at least one connecting element makes said refastenable side seam.

2. The process of claim 1, comprising cutting said second elastic sheet after connecting said end portions to said second elastic sheet by means of said respective connecting elements.

3. The process of claim 1, comprising temporarily spacing said first elastic sheet and said second elastic sheet from each other while said end portions are folded.

4. The process of claim 1, comprising folding said end portions by superimposing them onto respective portions of said first elastic sheet, wherein said folded end portions are configured to be part of distinct hygienic absorbent articles.

5. The process of claim 1, comprising hiding said respective connecting elements from said second elastic sheet while said end portions are folded.

6. The process of claim 1, comprising moving away said first elastic sheet from said second elastic sheet before cutting said first elastic sheet.

7. The process of claim 1, wherein performing the processes of cutting said first elastic sheet and of folding said end portions comprises performing such processes along a curved path.

8. The process of claim 1, comprising cutting said first elastic sheet along a cutting line passing through said at least one connecting element.

9. The process of claim 1, comprising cutting said first elastic sheet along a cutting line positioned between two respective connecting elements adjacent to each other.

* * * * *